(12) United States Patent
Jonsson et al.

(10) Patent No.: US 10,617,537 B2
(45) Date of Patent: Apr. 14, 2020

(54) VACUUM ASSISTED SUSPENSION SYSTEM

(71) Applicant: OSSUR HF, Reykjavik (IS)

(72) Inventors: Grimur Jonsson, Reykjavik (IS); Bjarni Gunnarsson, Reykjavik (IS); Olafur Freyr Halldorsson, Reykjavik (IS); David Sandahl, Reykjavik (IS)

(73) Assignee: OSSUR HF, Reykjavik (IS)

( * ) Notice: Subject to any disclaimer, the term of this patent is extended or adjusted under 35 U.S.C. 154(b) by 128 days.

(21) Appl. No.: 15/885,068

(22) Filed: Jan. 31, 2018

(65) Prior Publication Data

US 2018/0153715 A1 Jun. 7, 2018

Related U.S. Application Data

(63) Continuation of application No. 14/940,403, filed on Nov. 13, 2015, now Pat. No. 9,889,025, which is a continuation of application No. 13/766,086, filed on Feb. 13, 2013, now Pat. No. 9,198,780.

(60) Provisional application No. 61/693,384, filed on Aug. 27, 2012, provisional application No. 61/598,536, filed on Feb. 14, 2012.

(51) Int. Cl.
*A61F 2/80* (2006.01)
*A61F 2/78* (2006.01)
*A61F 2/66* (2006.01)
*A61F 2/74* (2006.01)

(52) U.S. Cl.
CPC .................. *A61F 2/80* (2013.01); *A61F 2/66* (2013.01); *A61F 2002/742* (2013.01); *A61F 2002/802* (2013.01); *A61F 2002/805* (2013.01)

(58) Field of Classification Search
CPC ........ A61F 2/78; A61F 2/80; A61F 2002/802; A61F 2/66
See application file for complete search history.

(56) References Cited

U.S. PATENT DOCUMENTS 708,685 A 9/1902 White
980,457 A 1/1911 Toles
(Continued)

FOREIGN PATENT DOCUMENTS

AU 670631 B2 7/1996
BE 675 386 A 5/1966
(Continued)

OTHER PUBLICATIONS

International Search Report from PCT Application No. PCT/US2015/044434, dated Oct. 8, 2015.
(Continued)

*Primary Examiner* — Bruce E Snow
(74) *Attorney, Agent, or Firm* — Workman Nydegger

(57) ABSTRACT

A vacuum assisted suspension system includes a prosthetic foot and a pump mechanism connected to the foot and fluidly couplable to a prosthetic socket. The pump mechanism includes an elongate pivoting member rotatable relative to the prosthetic foot about a joint and including a distal recess. A piston is connected to the foot and is movably received in the recess. A fluid chamber is defined between the piston and the interior of the recess. When no weight is placed on the foot a volume of the fluid chamber is zero or near-zero and when weight of a user is placed on the prosthetic foot the pivoting member rotates away from the piston and expands the volume of the fluid chamber to draw fluid into the fluid chamber from the prosthetic socket.

19 Claims, 6 Drawing Sheets

(56) References Cited

U.S. PATENT DOCUMENTS

| | | |
|---|---|---|
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Andersen |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,947,156 A | 3/1976 | Becker |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A | 5/1994 | Fay et al. |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,885,509 A | 3/1999 | Kristinsson |
| 5,888,216 A | 3/1999 | Haberman |
| 5,888,230 A | 3/1999 | Helmy |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,099,572 A | 8/2000 | Mosler et al. |
| 6,117,117 A | 9/2000 | Mauch |
| 6,136,039 A | 10/2000 | Kristinsson et al. |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 | 11/2003 | Caspers |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,001,563 B2 | 2/2006 | Janusson et al. |
| 7,025,792 B2 | 4/2006 | Collier |
| 7,025,793 B2 | 4/2006 | Egilsson |
| 7,105,122 B2 | 9/2006 | Karason |
| 7,118,602 B2 | 10/2006 | Bjarnason |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush et al. |
| 7,909,884 B2 | 3/2011 | Egilsson et al. |

(56) References Cited

U.S. PATENT DOCUMENTS

| | | |
|---|---|---|
| 7,922,775 B2 | 4/2011 | Caspers |
| 7,947,085 B2 | 5/2011 | Haines et al. |
| 7,993,413 B2 | 8/2011 | Perkins et al. |
| 8,007,543 B2 | 8/2011 | Martin |
| 8,034,120 B2 | 10/2011 | Egilsson et al. |
| 8,052,760 B2 | 11/2011 | Egilsson et al. |
| 8,080,065 B2 | 12/2011 | Scussel et al. |
| 8,097,043 B2 | 1/2012 | Egilsson |
| 8,097,766 B2 | 1/2012 | Carlson et al. |
| 8,114,167 B2 | 2/2012 | Caspers |
| 8,298,294 B2 | 10/2012 | Kaltenborn et al. |
| 8,317,876 B2 | 11/2012 | Mosler |
| 8,343,233 B2 | 1/2013 | Perkins et al. |
| 8,523,951 B2 | 9/2013 | Kania |
| 8,894,719 B2 | 11/2014 | Egilsson et al. |
| 8,911,506 B2 | 12/2014 | Egilsson et al. |
| 8,956,422 B2 | 2/2015 | Halldorsson |
| 8,961,618 B2 | 2/2015 | Lecomte et al. |
| 9,017,421 B2 | 4/2015 | Lecomte et al. |
| 9,044,348 B2 | 6/2015 | Halldorsson et al. |
| 9,056,022 B2 | 6/2015 | Egilsson et al. |
| 9,060,885 B2 | 6/2015 | Egilsson et al. |
| 9,066,821 B2 | 6/2015 | Egilsson et al. |
| 9,066,822 B2 | 6/2015 | Caldwell et al. |
| 9,072,617 B2 | 7/2015 | Halldorsson et al. |
| 9,198,780 B2 | 12/2015 | Jonsson et al. |
| 9,259,332 B2 | 2/2016 | Danzig et al. |
| 9,757,256 B2 | 9/2017 | Sandahl |
| 9,943,421 B2 | 4/2018 | Sverrisson et al. |
| 2001/0005798 A1 | 6/2001 | Caspers |
| 2001/0016781 A1 | 8/2001 | Caspers |
| 2002/0052663 A1 | 5/2002 | Herr et al. |
| 2002/0087215 A1 | 7/2002 | Caspers |
| 2002/0091449 A1 | 7/2002 | Caspers et al. |
| 2002/0103545 A1 | 8/2002 | Arbogast et al. |
| 2002/0128580 A1 | 9/2002 | Carlson et al. |
| 2003/0191539 A1 | 10/2003 | Caspers |
| 2004/0024322 A1 | 2/2004 | Caspers |
| 2004/0030411 A1 | 2/2004 | Caspers |
| 2004/0049290 A1 | 3/2004 | Bedard |
| 2004/0064195 A1 | 4/2004 | Herr |
| 2004/0122528 A1 | 6/2004 | Egilsson |
| 2004/0163278 A1 | 8/2004 | Caspers et al. |
| 2004/0181290 A1 | 9/2004 | Caspers |
| 2004/0236434 A1 | 11/2004 | Carstens |
| 2004/0260403 A1 | 12/2004 | Patterson et al. |
| 2005/0131324 A1 | 6/2005 | Bledsoe |
| 2005/0131549 A1 | 6/2005 | Caspers |
| 2005/0143838 A1 | 6/2005 | Collier |
| 2005/0240282 A1 | 10/2005 | Rush et al. |
| 2005/0267603 A1 | 12/2005 | Lecomte et al. |
| 2006/0074493 A1 | 4/2006 | Bisbee, III et al. |
| 2006/0212130 A1 | 9/2006 | Collier |
| 2006/0212131 A1 | 9/2006 | Curtis |
| 2006/0224246 A1 | 10/2006 | Clausen et al. |
| 2007/0005149 A1 | 1/2007 | Egilsson et al. |
| 2007/0043316 A1 | 2/2007 | Carlson et al. |
| 2007/0050044 A1 | 3/2007 | Haynes et al. |
| 2007/0055383 A1 | 3/2007 | King |
| 2007/0112440 A1 | 5/2007 | Perkins et al. |
| 2007/0196222 A1 | 8/2007 | Mosler et al. |
| 2007/0204487 A1 | 9/2007 | Clough |
| 2007/0213839 A1 | 9/2007 | Nachbar |
| 2008/0086218 A1 | 4/2008 | Egilsson |
| 2008/0147202 A1 | 6/2008 | Danzig et al. |
| 2008/0147204 A1 | 6/2008 | Ezenwa |
| 2008/0243266 A1 | 10/2008 | Haynes et al. |
| 2008/0269911 A1 | 10/2008 | Street et al. |
| 2008/0269912 A1 | 10/2008 | Gobbers et al. |
| 2009/0036998 A1 | 2/2009 | Finlinson et al. |
| 2009/0132056 A1 | 5/2009 | Kania |
| 2009/0157196 A1 | 6/2009 | Danzig et al. |
| 2009/0198346 A1 | 8/2009 | Perkins et al. |
| 2009/0204229 A1 | 8/2009 | Mosler et al. |
| 2009/0281637 A1 | 11/2009 | Martin |
| 2010/0070051 A1 | 3/2010 | Carstens |
| 2010/0087931 A1 | 4/2010 | Bogue |
| 2010/0106260 A1 | 4/2010 | Phillips |
| 2010/0262261 A1 | 10/2010 | Laghi |
| 2010/0312359 A1 | 12/2010 | Caspers |
| 2010/0312360 A1 | 12/2010 | Caspers |
| 2010/0331749 A1 | 12/2010 | Powaser |
| 2011/0035027 A1 | 2/2011 | McCarthy |
| 2011/0046748 A1 | 2/2011 | Martin et al. |
| 2011/0060421 A1 | 3/2011 | Martin et al. |
| 2011/0071649 A1 | 3/2011 | McKinney |
| 2011/0087142 A1 | 4/2011 | Ravikumar et al. |
| 2011/0125291 A1 | 5/2011 | Tompkins et al. |
| 2011/0130846 A1 | 6/2011 | Kampas et al. |
| 2011/0184532 A1 | 7/2011 | Tompkins |
| 2011/0202143 A1 | 8/2011 | Caspers |
| 2011/0270413 A1 | 11/2011 | Haynes |
| 2011/0295386 A1 | 12/2011 | Perkins et al. |
| 2012/0000092 A1 | 1/2012 | Ingvarsson et al. |
| 2012/0022667 A1 | 1/2012 | Accinni et al. |
| 2012/0035520 A1 | 2/2012 | Ingimudarson et al. |
| 2012/0123559 A1 | 5/2012 | Mosler et al. |
| 2012/0173000 A1 | 7/2012 | Caspers |
| 2012/0173001 A1 | 7/2012 | Caspers |
| 2012/0191217 A1 | 7/2012 | Mackenzie |
| 2013/0053982 A1 | 2/2013 | Halldorsson |
| 2013/0096694 A1 | 4/2013 | Caldwell et al. |
| 2013/0211544 A1 | 8/2013 | Jonsson et al. |
| 2013/0282142 A1 | 10/2013 | Perkins et al. |
| 2013/0289741 A1 | 10/2013 | Halldorsson et al. |
| 2014/0243997 A1 | 8/2014 | Clausen et al. |
| 2014/0249648 A1 | 9/2014 | Sandahl |
| 2016/0120665 A1 | 5/2016 | Muller |
| 2016/0199202 A1 | 7/2016 | Jonasson et al. |
| 2016/0346100 A1 | 12/2016 | Sverrisson et al. |
| 2017/0056210 A1 | 3/2017 | Jonasson et al. |
| 2018/0055659 A1 | 3/2018 | Sandahl et al. |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685 861 C | 12/1939 |
| DE | 745 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | H07-155343 A | 6/1995 |
| SE | 88-01686 A | 3/1989 |

(56) References Cited

FOREIGN PATENT DOCUMENTS

| | | | |
|---|---|---|---|
| SU | 1667855 | A1 | 8/1991 |
| SU | 1771722 | C | 10/1992 |
| SU | 1812982 | A3 | 4/1993 |
| SU | 1821177 | A1 | 6/1993 |
| WO | 84/00881 | A1 | 3/1984 |
| WO | 95/05792 | A1 | 3/1995 |
| WO | 96/21405 | A1 | 7/1996 |
| WO | 98/04218 | A1 | 2/1998 |
| WO | 98/55055 | A1 | 12/1998 |
| WO | 99/05991 | A2 | 2/1999 |
| WO | 99/65434 | A1 | 12/1999 |
| WO | 00/03665 | A1 | 1/2000 |
| WO | 00/74611 | A2 | 12/2000 |
| WO | 01/54631 | A1 | 8/2001 |
| WO | 01/70147 | A2 | 9/2001 |
| WO | 02/26158 | A2 | 4/2002 |
| WO | 02/065958 | A2 | 8/2002 |
| WO | 02/067825 | A2 | 9/2002 |
| WO | 02/080813 | A2 | 10/2002 |
| WO | 03/077797 | A2 | 9/2003 |
| WO | 03/099173 | A1 | 12/2003 |
| WO | 03/099188 | A1 | 12/2003 |
| WO | 2005/039444 | A2 | 5/2005 |
| WO | 2005/105000 | A1 | 11/2005 |
| WO | 2006012820 | A1 | 2/2006 |
| WO | D071077 | | 10/2008 |
| WO | 2010/141960 | A2 | 12/2010 |
| WO | 2011/035099 | A1 | 3/2011 |
| WO | 2012010309 | A1 | 1/2012 |
| WO | 2012177965 | A1 | 12/2012 |
| WO | 2014126554 | A1 | 8/2014 |
| WO | 2014194998 | A1 | 12/2014 |
| WO | 2016112030 | A1 | 7/2016 |

OTHER PUBLICATIONS

International Search Report from PCT Application No. PCT/US2015/041089, dated Oct. 5.2015.
International Search Report from corresponding PCT Application No. PCT/US2016/033915, dated Jul. 29, 2016.
International Search Report from PCT Application No. PCT/US2016/012215, dated May 23, 2016.
International Search Report from PCT Application No. PCT/US2016/033707, dated Jul. 29, 2016.
Brochure, "Sometimes Less is More, Harmony P3" Otto Bock, 12 pages. Available at, http://www.ottobock.com/cps/rde/xbcr/ob_es/646A303-EN-01-1001w.pdf', dated 2012.
Information Guide, Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf', dated 2012.
Brochure,"Harmony Certification Course Manual," Original Harmony Pump, 42 pages. Availiable at, http://academy.ottobockus.com/videos/harmony/data/downloads/harmony%20course%20manual%202013.pdf. Dated 2013.
Brochure, Harmony P2 & HD, 2 pages. Available at http://www.ottobock.com/cps/rde/xchg/ob_us_en/hs.xsl/14904.html?id=4641. Dated 2012.
International Search Report from corresponding International PCT Application No. PCT/US2013/025849, dated Jun. 4, 2013.
International Search Report and Written Opinion from corresponding International PCT Application No. PCT/US2013/038668, dated Aug. 7, 2013.
Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.
International Search Report and Written Opinion from corresponding International PCT Application No. PCT/US2014/019218, dated May 9, 2014.

FIG. 2
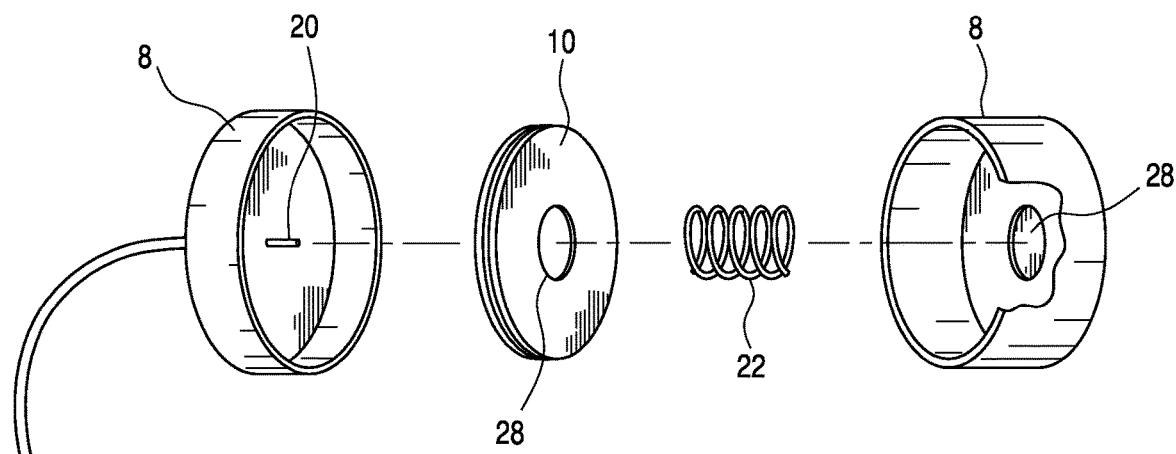
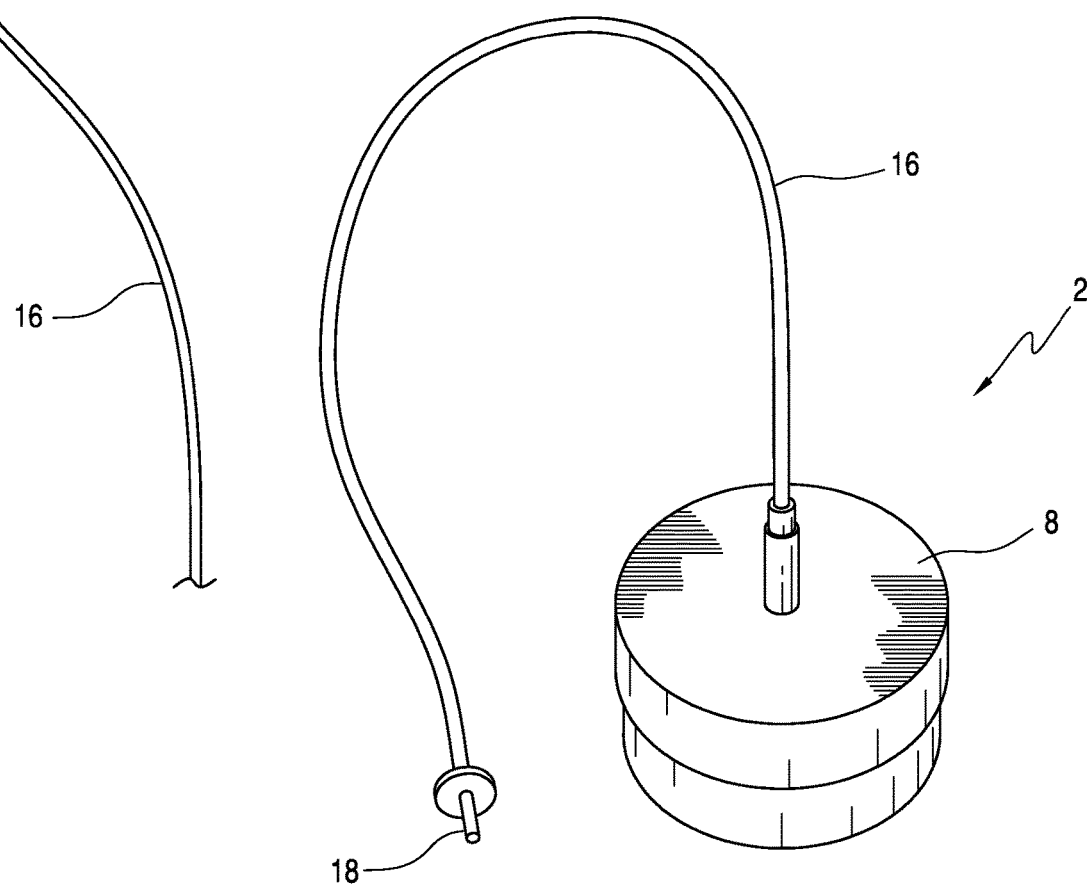
FIG. 3

VACUUM ASSISTED SUSPENSION SYSTEM

FIELD OF ART

The disclosure relates to the field of prosthetic devices, and more particularly to a vacuum assisted suspension system.

BACKGROUND

In the field of prosthetics, an amputee can attach a prosthetic limb to the residual limb via a socket of the prosthesis using a variety of mechanical attachment or suspension mechanisms. A suspension system usually relies on creating a vacuum or negative air pressure in the space between the socket and the surface of the residual limb. A seal is created by covering the brims of the socket with a sleeve. The seal for the vacuum space, however, is not airtight, so air may leak into the vacuum space weakening the attachment.

As a result, there is a need for a system which can create and maintain negative air pressure during use.

In some prosthetic systems, when weight is applied to a prosthetic attachment such as a prosthetic foot, the applied weight causes the vacuum pump to decrease the volume of the pump and expel air out of the pump. Then, when the compressive force is removed, the pump expands and draws air out of the vacuum space to create a vacuum effect. In these types of systems, the system relies on a complete compression of the pump in expelling air in each cycle to use the pump to its maximum capacity. It is difficult for complete compression to occur in every cycle using the gait of a user as the compressive force since the impact and displacement of the pump may not be consistent and can vary between users.

SUMMARY

The challenges of known vacuum assisted suspension systems are addressed in accordance with embodiments of the disclosure providing a vacuum assisted suspension system including a vacuum pump.

In accordance with an embodiment of the method of creating vacuum in a prosthetic socket, a compressive force is applied to a first end of a compression transfer element by applying weight or force to a prosthetic device or limb. The force applied on the first end of the compression transfer element causes the volume of the fluid chamber to increase via a second end of the compression transfer element connected to a movable wall of the fluid compartment, and fluid is drawn into the fluid chamber from a socket space or cavity through an input port upon an increase in the volume of the fluid chamber. When the compressive force is removed the absence of the compressive force enables the volume of the fluid chamber to decrease thereby expelling fluid out of the fluid chamber through an output port.

Preferably, the volume of the fluid chamber is zero or approximately zero in the absence of a compressive force. Having a compressive force increase the volume of the fluid chamber from zero and the absence of the compressive force enable a return to a volume of zero or near zero has been found to be advantageous since each pump cycle is fully utilized by fully expelling all or substantially all fluid drawn into the fluid compartment. This type of method and prosthetic system more effectively and efficiently uses the vacuum pump to increase or the vacuum or negative pressure within a sealed socket cavity. Smaller fluctuations in negative pressure are also achieved.

In various embodiments of the vacuum assisted suspension system described herein, the system includes a prosthetic foot, a prosthetic socket, an elongate compression transfer element connected to the prosthetic foot, and a vacuum pump connected to the prosthetic socket and the compression transfer element. The vacuum pump includes a housing defining an enclosed space to receive a fluid, at least one wall of the housing and at least one movable wall defining a fluid compartment, and the at least one movable wall is connected to the compression transfer element. The compression transfer element causes the at least one movable wall of the fluid compartment to move and increase the volume of the fluid compartment in response to a compressive force on the prosthetic foot to draw in fluid from the prosthetic socket, and in the absence of a compressive force, the movable wall is arranged to shift in a direction decreasing the volume of the fluid compartment thereby expelling fluid from the fluid compartment.

In accordance with an embodiment of the vacuum pump, the enclosed space in the housing can be divided into a fluid compartment and a non-fluid compartment by a movable wall. The movable wall forms a seal with the interior wall of the housing and reciprocates within the housing to change the volume of the compartments upon application and removal of a compressive force. An embodiment of the vacuum pump can include a spring element which is compressed by the movable wall upon application of a compressive force and configured to expand in the absence of force on the movable wall to assist in expelling our out of the fluid compartment. The compression transfer element may be in the form of a wire which transfers force from a prosthetic foot to the movable wall by using pins on each end of the compression transfer element which are displaced by a compressive force.

In an embodiment of the system, a tensioned cable connected between a prosthetic foot and the housing of the vacuum is arranged to enable a spring element to expand upon application of a compressive force to the tensioned cable thereby increasing the volume of the fluid chamber. When the compressive force is removed or is absent, the tensioned cable compresses the spring causing the volume of the fluid compartment to decrease.

In accordance with an embodiment of the system, the system includes a vacuum pump having a housing comprising a pair of opposed movable walls with the fluid compartment defined by the movable walls and the elastomeric sidewalls. The opposed walls each include a wall extension to translate a compressive force into an increase in the volume of the fluid compartment. One of the wall extensions is connected to a proximal portion of the prosthetic foot and the second wall extension is connected to a distal portion of the prosthetic foot such as a heel portion.

In an embodiment of the system, the system includes a vacuum pump comprising a base member and a pivoting member pivotally connected to each other at a first end by a joint. At a second end of the vacuum pump, opposite the joint end, a protruding wall is arranged on the base member opposite a recess of the pivoting member. The protruding wall can reciprocate within the recess of the pivoting member, and form a seal with the walls of the recess. The protruding wall and the recess form a fluid chamber for the vacuum pump. The base member is connected to the prosthetic foot and the pivoting member has a connector on the joint end to connect to a pylon or socket of a residual limb. When the base member and pivoting member rotate away from each other, the volume of the fluid compartment is increased to draw in fluid from the socket cavity, and when the base member and pivoting member rotate towards each other, the volume of the fluid compartment is decreased to expel fluid from the fluid compartment.

The numerous advantages, features and functions of the various embodiments of the vacuum assisted suspension system will become readily apparent and better understood in view of the following description and accompanying drawings. The following description is not intended to limit the scope of the prosthetic system, but instead merely provides exemplary embodiments for ease of understanding.

BRIEF DESCRIPTION OF THE DRAWINGS

The vacuum assisted suspension system is described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

FIG. 2 is an exploded view of the vacuum pump in FIG. 1.

FIG. 3 shows a view of the vacuum pump of FIG. 2 in assembled form.

DETAILED DESCRIPTION OF VARIOUS EMBODIMENTS

Figure 1:
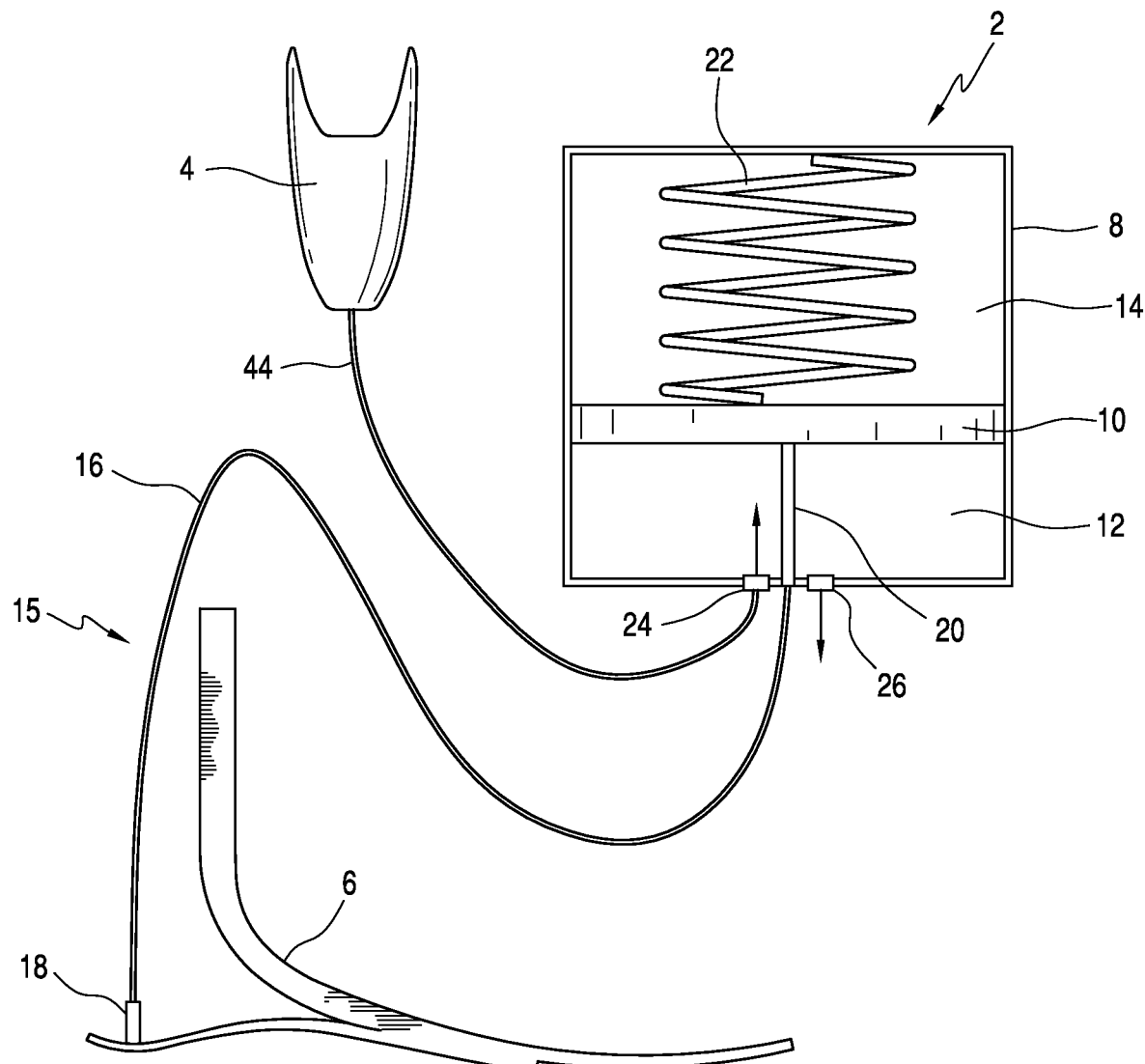
FIG. 1 is a schematic illustration of a vacuum assisted suspension system according to a first embodiment.

A better understanding of different embodiments of the vacuum assisted suspension system may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this disclosure to possess a described meaning, there is no intent to limit the meaning of such term, either expressly or indirectly, beyond its plain or ordinary meaning Any element in a claim that does not explicitly state "means for" performing a specified function, or "step for" performing a specific function, is not to be interpreted as a "means" or "step" clause as specified in 35 U.S.C. § 112, paragraph 6.

The anatomical terms described herein are not intended to detract from the normal understanding of such terms as readily understood by one of ordinary skill in the art of prosthetics. For example, the term "distal" is used to denote the portion or end of a limb that is farthest from the central portion of the body. The term distal is the opposite of "proximal" which is used to denote that the end or portion of the limb is nearer to the central portion of the body.

Embodiments of a vacuum assisted suspension system include a vacuum pump having a fluid connection with a socket, and the vacuum pump assists in creating a vacuum between a residual limb and the socket by pumping fluid out of the socket. The fluid is pumped out of the socket when the user puts his weight on a prosthetic foot such as upon a heel strike. The compressive force of the heel strike causes a compression transfer element of the pump to increase the volume of a fluid chamber in the pump. The increase in volume of the pump draws in fluid from the vacuum space between the residual limb and the socket of a prosthetic limb. In this manner, the pump decreases the air pressure within the vacuum space causing a vacuum effect.

After the compressive force is removed, for example, during toe-off and the swing phase of gait, the volume of the fluid chamber in the pump is decreased. The connection between the vacuum space of the socket and the pump may have a one-way valve, so all of the air within the volume of the pump is expelled out of an outlet to another space or to atmosphere. The inlet can be provided with a one-valve so that the vacuum space of the socket is the only source of air or fluid.

This method of producing a vacuum effect in the prosthetic socket is advantageous over prior method of compressing the pump to expel air and decompressing the pump to draw in air. The method described herein achieves smaller fluctuations in air pressure, so the difference between the greatest pressure and least pressure in the vacuum space is less in the method described herein compared to prior art methods.

The efficiency of the pump is determined partially by how effectively the volume of the fluid chamber is reduced. Since the pump returns to the original state of zero or near-zero volume at the beginning or end of each cycle, the volume of the fluid chamber is determined by the degree of compressive force applied to the pump. In the method described herein, all fluid drawn into the pump is expelled afterwards, thus, fully utilizing each cycle. Additionally, the method described herein may be implemented using a pump that does not have any spring type elements which may affect the bio-mechanical function of the prosthetic system.

The benefits of using a vacuum suspension system include increased blood flow to the residual limb since there is less pressure on the residual limb. The vacuum suspension system also reduces volume fluctuations of the residual limb, and wounds on the residual limb heal faster. The vacuum assisted suspension system allows for increased proprioception and reduced pistoning since there is a better attachment between the socket and the residual limb. The socket trim lines can also be lowered with a vacuum suspension system resulting in a lighter, smaller prosthetic system.

It may also be beneficial to produce hypobaric pressure below a certain level in the socket. This may be achieved using a seal between the residual limb and the socket, instead of the conventional sealing method of using a sleeve to form an airtight connection between the residual limb and the proximal end of the socket. The seal may be provided as in an exemplary prosthetic liner described in U.S. Pat. No. 8,034,120 issued Oct. 11, 2011 incorporated herein by reference and belonging to the assignee of this disclosure.

The benefit of using, for example a liner having a seal, is to reduce the volume of air to be drawn out of the socket and therefore, a better suspension may be achieved in a shorter time period. Using a silicone liner with integrated seal also provides the added benefit that the hypobaric region is not directly applied to the skin.

The various embodiments of the vacuum assisted suspension system will now be described with respect to the figures.

FIG. 1 is a schematic illustration of an embodiment of a vacuum assisted suspension system. FIG. 1 shows a cross-sectional view of an exemplary embodiment of a vacuum pump 2 and the connections of the vacuum pump 2 to a socket 4 and a prosthetic foot 6. The vacuum pump 2 has a housing 8 which forms an enclosed interior space including a fluid chamber 12 and a non-fluid chamber 14. The chambers 12 and 14 are separated by a movable wall 10 which forms a seal with the sides of the housing 8. One side of the movable wall 10 forms part of the fluid chamber 12 and the opposite side of the movable wall 14 forms part of the non-fluid chamber 14.

A compression transfer element 15 is connects to the housing 8 of the vacuum pump 2 and to the prosthetic foot 6. The compression transfer element 15 includes a wire 16 which has a first pin 18 on the end attached to the heel portion of the prosthetic foot 6 and a second pin 20 on the end connected to the housing 8. The second pin 20 enters the fluid chamber 12 through an opening in the housing 8 to adjust the position of the movable wall 10 and connects with the side of the movable wall 10 which forms the fluid chamber 12. The wire 16 may be a flexible wire placed within a tubular casing which forms an airtight connection between the wire 16, the second pin 20, the housing 8 including the fluid chamber 12. The opening in the housing 8 for the second pin 20 may also be provided with a sealer such as an elastomeric ring which simultaneously allows reciprocation of the second pin 20 through the opening while providing an airtight connection between compression transfer element 15 and the vacuum pump 2. Alternatively, the compression transfer element 15 may be a stiff wire within a tubular casing. The compression transfer element 15 translates a compressive force into a force applied to the movable wall 10 to cause the movable wall 10 to reciprocate in the housing 8.

A compressive force can be a force created during gait on the prosthetic foot, in particular, by applying weight to a portion of the prosthetic foot 6. In an embodiment of the system, the compressive force is created upon heel strike when the user applies weight to the heel area of the prosthetic foot 6 to which one end of the compression transfer element is attached. The compression transfer element 15 translates the heel strike force into a force to cause the movable wall 10 to reciprocate.

In the absence of a compressive force, the movable wall 10 rests on the housing surface having an input port 24 and output port 26 such that the fluid chamber 12 has zero or near zero volume. The input port 24 and output port 26 may be positioned anywhere on the surface of the housing 8. It is preferred that the ports 24 and 26 be placed opposite the movable wall 10 for the most efficient pumping mechanism and on the same side as the opening for the second pin 20.

To create or increase the vacuum effect, a user places his weight on the prosthetic foot 6, which creates a compressive force that causes the first pin 18 to push on the wire 16 and slide into the tubular casing. When the first pin 18 pushes on the wire 16, the wire 16 is displaced and pushes on the second pin 20. The second pin 20 applies a force which may be substantially perpendicular to the movable wall 10 to increase the volume of the fluid chamber 12. Due to the increase in the volume of the fluid chamber 12, fluid is drawn into the fluid chamber 12 via an input port 24 from the socket 4 through a tube 44

When the compressive force is removed, the movable wall 10 returns to its original state of resting on the housing surface which simultaneously returns the fluid chamber 12 to its original state of approximately zero volume. When the volume of the fluid chamber 12 is decreasing, fluid drawn in from the socket 4 previously is now forced out of the output port 26. The output port 26 is provided with a one-way valve which only allows fluid out of the output port 26. The input port 24 may also have a one-way valve which prevents fluid in the fluid chamber 12 from returning to the socket and only allows fluid to enter the fluid chamber 12.

The pump 2 may optionally have a spring element 22 in the non-fluid chamber which assists in returning the fluid chamber 12 to a volume of zero or approximately zero. The spring element 22 may be substantially perpendicular to the movable wall 10 and is compressed when the fluid chamber 12 is enlarged. In other words, the direction of compression and expansion of the spring element is arranged to be perpendicular to the movable wall 10. When the compressive force is removed, the spring element 22 decompresses and pushes the movable wall 10. The addition of a spring element 22 increases the efficiency of the pump by allowing the pump to more quickly decompress due to the added force on the movable wall 10 provided by the spring element 22. The spring element 22 may be a coil or a spring, or formed from an elastomeric material.

In this manner, hypobaric pressure may be created or enhanced in the space enclosed by the residual limb and socket 4.

FIG. 2 is an exploded view of the embodiment of the vacuum pump 2 in FIG. 1. The pump housing 8 in this embodiment is shown to be formed of two pieces. The pump housing 8 may be formed of a single continuous housing. Further, while the vacuum pump housing 8 is shown to have a cylindrical shape, the pump housing 8 may take any form including any polygonal prism such as a rectangular prism. The movable wall 10, as seen in FIG. 2, has a circular shape corresponding to the base shape of the interior volume which is cylindrical in this embodiment. Similar to the vacuum pump housing 8, the movable wall 10 may have a variety shapes depending on the shape of the enclosed interior space of the housing 8. The shape of the movable wall 10 should correspond to the base shape of the housing 8 to create two completely separate chambers. The movable wall 10 may also be outlined with an elastomeric material to create an airtight partition between the fluid chamber 12 and the non-fluid chamber 14 while still allowing the movable wall 10 to easily reciprocate between the two chambers 12 and 14.

The input and output ports are not shown in this view. The spring element 22 is arranged between one side of the movable wall 10 and the housing 8. The spring element 22 may be received in corresponding recesses 28 on the movable wall 10 and housing 8 to maintain the positioning of the spring element 22 within the vacuum pump 2.

Because the vacuum pump housing 8 may take such a large variety of shapes, the vacuum pump 2 can be placed in numerous locations on the prosthetic foot. Further, the ability of the vacuum pump 2 to create a negative pressure effect is not limited by the size of any cavity in which the vacuum pump 2 may be placed. This allows the vacuum pump to be compatible with a wide range of prosthetic foot forms. The vacuum pump 2 also adds minimal weight to the prosthetic foot 6.

FIG. 3 shows the embodiment of FIG. 2 assembled with the first pin 18, the wire 16 within a casing and the outer housing 8 of the vacuum pump 2.

The wire 16 has a housing connector, and the housing 8 has a corresponding compression transfer element connector. The attachment between the compression transfer element 15 and the housing 8 may be a threaded attachment or interlocking connector or other types of attachments known in the art.

The wire 16 of the compression transfer element 15 may be made of any type of material which would provide the compression transfer element 15 with some rigidity and stiffness including metal, plastic, or fiberglass. The outer tubular casing for the wire 16 may be made of a variety of materials including plastic or an elastomeric material.

Additionally, the compression transfer element 15 may take the form of a shaft which is connected to the heel section of the prosthetic foot. The vertical displacement of the heel caused upon heel strike would generate the compressive force acting on the pump.

The vacuum pump may also be placed inside the prosthetic foot. During the stance phase of gait, the weight of the user would apply a compressive force to the pump to increase the volume of the fluid chamber and draw in air from the socket as similarly described above.

FIGS. 4-7 show other variations of the vacuum pump 2.

Figure 4:
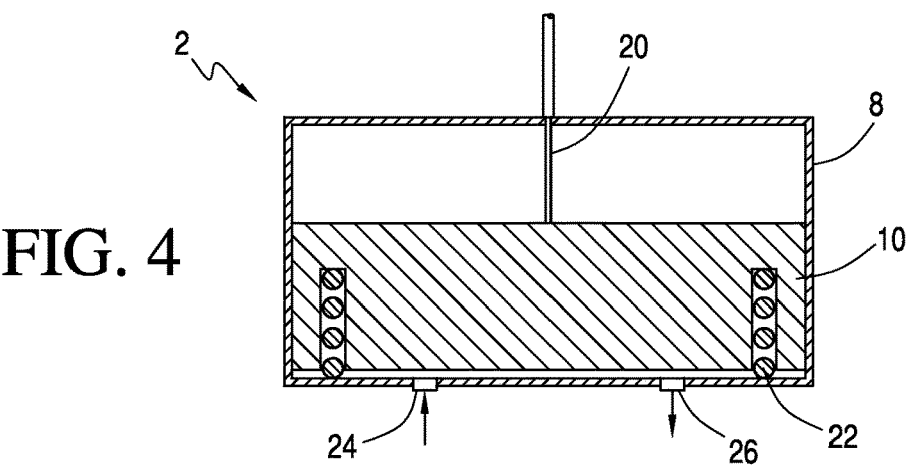
FIG. 4 shows a cross-sectional view of an embodiment of the vacuum pump.

FIG. 4 shows a movable wall 10 with a recess outlining the shape of the spring element 22 to receive the spring element 22 in the fluid compartment. For example, the spring element 22 may be cylindrical such that the recess is a circular indentation in the movable wall 10. The input port 24 and output port 26 are arranged on the side of the housing 8 opposite the side in which the second pin 20 enters the vacuum pump. The vacuum pump in FIG. 4 is shown in a compressed state with the second pin 20 extending from the wire 16 into the non-fluid compartment to push the movable wall 10 against the opposing side to expel fluid out of output port 26. Once pressure on the second pin 20 is released, the spring element 22 decompresses to push the movable wall 10 towards the pin receiving side of the housing 8 and draw fluid into the pump 2 through input port 24.

Figure 5:
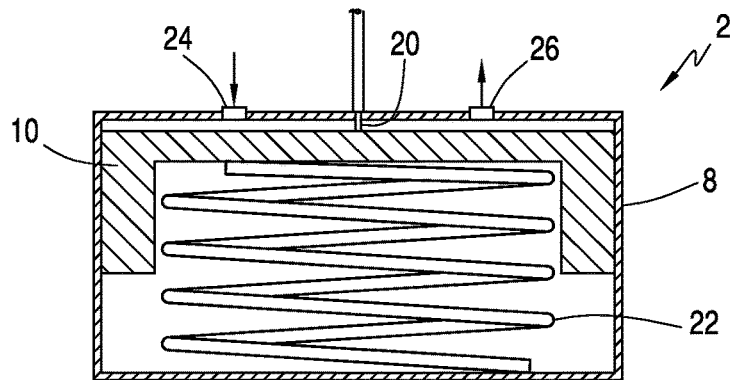
FIG. 5 is a cross-sectional view of another embodiment of the vacuum pump.

FIG. 5 shows another arrangement of the elements of the vacuum pump 2. In FIG. 5, the ports 24, 26 are arranged adjacent or on the same side of the housing 8 as the second pin 20 similar to the embodiment shown in FIGS. 1-3. The movable wall 10 in FIG. 5 is provided with a cylindrical recess having a depth to receive approximately half of the spring element 22 in its uncompressed state. When the second pin 20 receives pressure or force, the second pin 20 pushes the movable wall 10 towards the opposing wall until the movable wall 10 comes into contact with the housing 8. The second pin 20 extends into the fluid compartment and connects with the movable wall 10 on the fluid compartment side.

Figure 6:
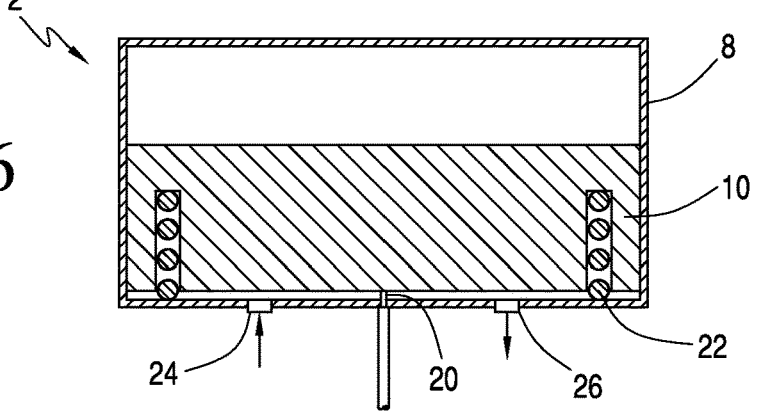
FIG. 6 shows a cross-sectional view of another embodiment of the vacuum pump.

FIG. 6 shows another embodiment of the vacuum pump 2. FIG. 6 is similar to the embodiment shown in FIG. 4, but the second pin 20 is arranged on the same side as the ports 24, 26. In this embodiment, the pin 20 can extend from wire 16 into the fluid compartment to push the movable wall 10 and draw in fluid through input port 24. The spring element 22 in the fluid compartment can serve the opposite effect of the pin 20 and pull the movable wall 10 towards the ports 24, 26 to expel air out of output port 26.

Figure 7:
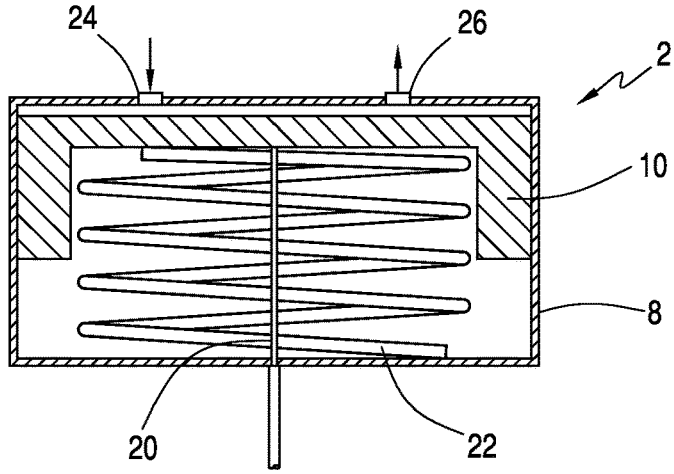
FIG. 7 shows a cross-sectional view of another embodiment of the vacuum pump.

FIG. 7 shows an embodiment of the vacuum pump 2 with elements similar to those of FIG. 5. In FIG. 7, the second pin 20 extends out of the wire 16 into the non-fluid compartment to push the moveable wall 10 towards the ports 24, 26. When pressure on the second pin 20 is released, the spring element 22 in the non-fluid compartment can serve to draw the moveable wall 10 away from the ports 24, 26 to draw in fluid into the pump 2 through input port 24.

Figure 8:
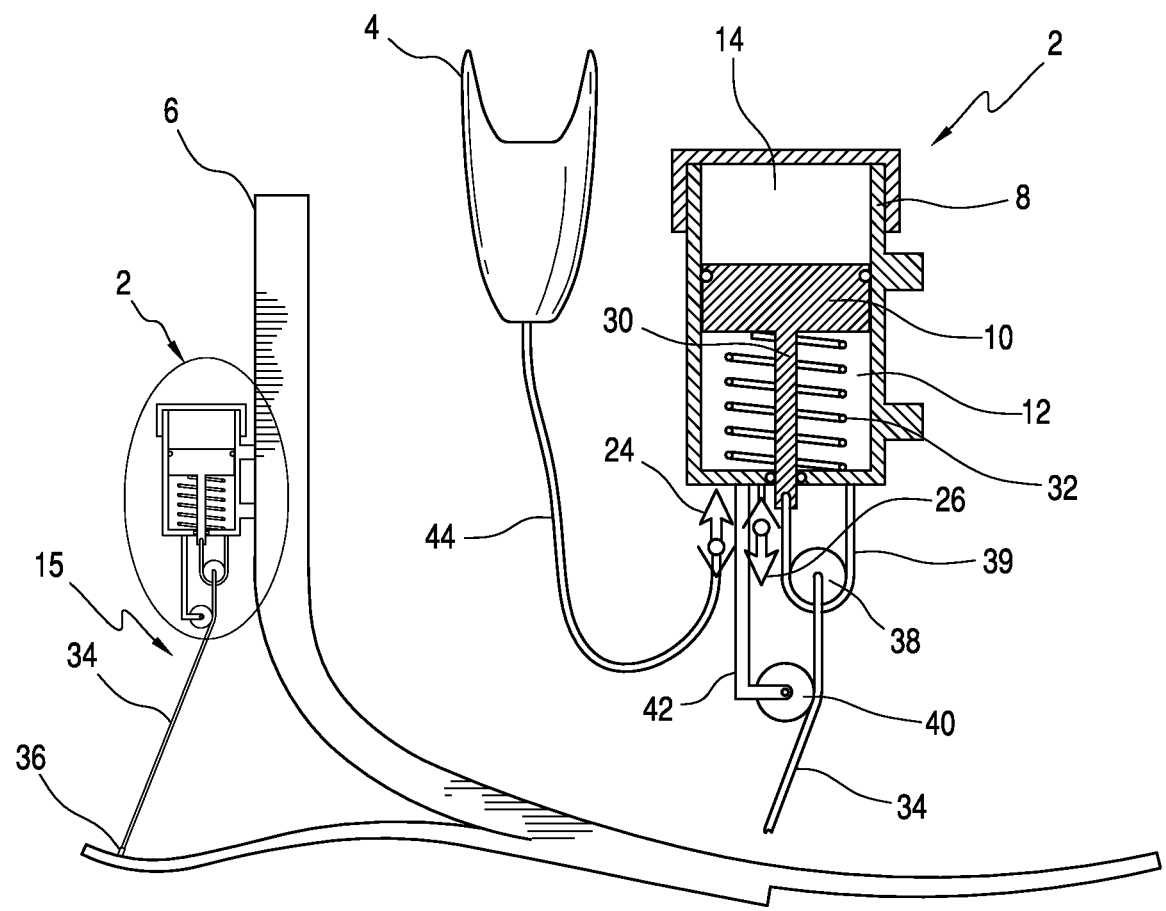
FIG. 8 shows a variation of the vacuum assisted suspension system.

FIG. 8 depicts a variation of the vacuum assisted suspension system. The vacuum assisted suspension system shown in FIG. 8 includes an enlarged cross-sectional view of the vacuum pump 2 as well as the connections between the pump 2, the socket 4, and prosthetic foot 6. Vacuum pump 2 has a housing 8 which may comprise two pieces. The two pieces may use a threaded connection to attach to each other. The housing 8 forms an interior enclosed space and within the interior enclosed space is a movable wall 10 which divides the enclosed space into a fluid chamber 12 and a non-fluid chamber 14. One side of the movable wall 10 forms the fluid chamber 12 and the opposite side forms the non-fluid chamber 14. The movable wall 10 reciprocates within the enclosed space to change the volume of the fluid chamber 12 and the non-fluid chamber 14. The vacuum pump 2 may be attached to the shank or the pylon of the prosthetic foot above the ankle area as shown in FIG. 8.

The compression transfer element 15 includes a tensioned cable or wire 34 having an end pin 38 which interacts with a protruding pin 30 of the movable wall 10 by pulling and releasing a wire loop 39. The protruding pin 30 is positioned on the side of the movable wall 10 forming part of the fluid chamber 12 and extends through the fluid chamber 12. The protruding pin 30 may extend outside of the housing 8 and the opening through which the protruding pin 30 reciprocates can be provided with a sealer such as an elastomeric ring to provide an airtight connection.

In the absence of a compressive force which is a force directed towards the vacuum pump 2, the tensioned cable 34 is taut and pulls the movable wall 10 towards the output port 26 which compresses the spring element 32 and changes the volume of the fluid chamber 12 to zero or approximately zero. Similar to the previous embodiment, the ports 24 and 26 may be placed anywhere on the surface of the housing 8 and are preferably placed opposite the movable wall 10.

When the user places his weight on the prosthetic foot, such as during a heel strike, the tension in the cable 34 is reduced allowing the spring element 32 to decompress and push the movable wall 10 away from input port 24 and output port 26. The cable 34 is attached to the heel portion of the prosthetic foot 6 by a cable anchor 36 at the distal end of the cable 34. The proximal end of the cable 34 has the end pin 38 which is located in the wire loop 39. The wire loop 39 is looped around the end pin 38 such that one end of the wire loop 39 is attached to the outside of the housing 8 and the other end of the wire loop 39 is attached to the protruding pin 30 of the movable wall 10. The end pin 38 of the cable 34 is located on the interior of the loop 39 acts like an adjustable weight for the movable wall 10 by applying weight on the middle portion of the loop 39 to pull or release the movable wall 10.

The compression transfer element 15 may include a cable guide 40 at the end of a pump arm 42 protruding from the bottom of the housing 8. The pump arm 42 may have a perpendicular extension at the distal end to have the general shape of an "L" with the cable guide 40 attached to the end of the perpendicular extension. The cable guide 40 positions the proximal end of the cable 34 to be substantially parallel to the protruding pin 30. The spring element 32 may coil or wrap around the protruding pin 30. The spring element 32 may be a spring or may be formed from an elastomeric material.

The alternative arrangements of elements of the vacuum pump 2 shown in FIG. 47 may also be used in the vacuum pump 2 of the second embodiment of the prosthetic system described herein. The protruding pin 30 may be used in FIGS. 4-7 instead of pin 20. A skilled person would have known how to adapt the various embodiments of the vacuum pump 2 to be used in the embodiments of the prosthetic system described herein.

Figures 9A, 9B:
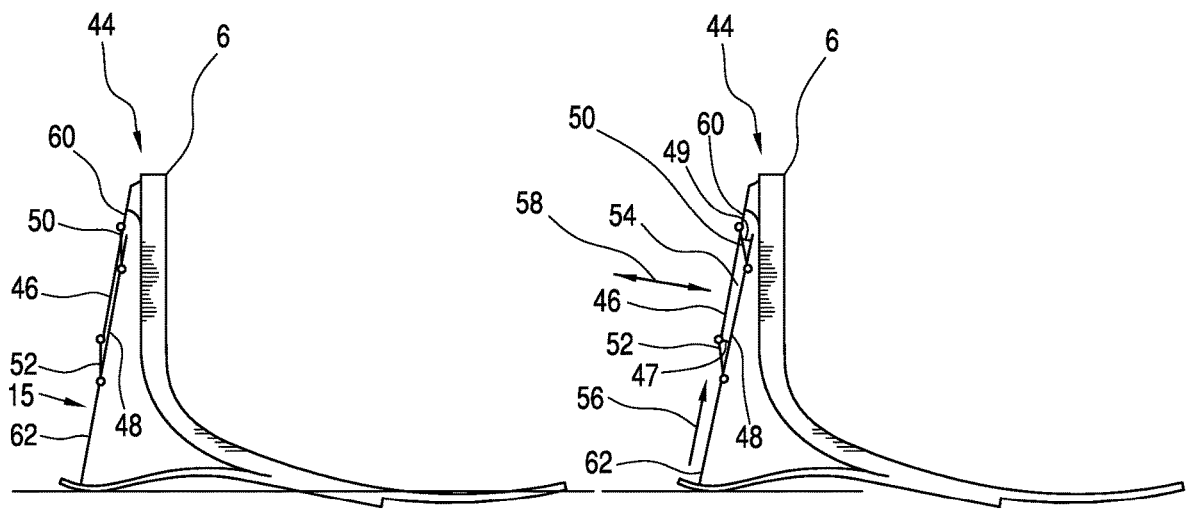
FIG. 9a shows an embodiment of the vacuum assisted suspension system in the absence of a compressive force.
FIG. 9b shows an embodiment of the vacuum assisted suspension system subjected to a compressive force.

FIGS. 9a and 9b show a different version of the vacuum assisted suspension system including the vacuum pump 44. FIG. 9a depicts the vacuum pump 44 in its original, decompressed state where the vacuum pump 44 is not subject to any compressive forces. In FIG. 9b, a compressive force 56 has been applied to the vacuum pump 44.

The housing 8 of vacuum pump 44 is formed of at least one pair of parallel movable walls 46 and 48 which are preferably rigid. Between the movable walls 46 and 48 is a fluid chamber 54 which may be formed of an elastomeric material. The fluid chamber 54 also has sidewalls 47, 49 which can be formed of the elastomeric material. The elastomeric material may have an accordion-like structure to enable the fluid chamber 54 to expand and contract. The housing of the vacuum pump 44 may have the shape of a rectangular prism when expanded.

The first movable wall 46 has an extension 60 which extends from the chamber area of the wall and attaches to proximal portion of the prosthetic foot 6. On the wall extension 60, one end of a first hinge 50 is connected to the first movable wall 46 outside of the fluid chamber area. The second end of the first hinge 50 is connected diagonally to the second movable wall 48 in the fluid chamber area of the second movable wall 48. The second hinge 52 is attached to the distal end of the first movable wall 46, and the wall extension 62 of the second movable wall 48. The second wall 48 has a distal extension 62 which connects to the heel of the prosthetic foot. As shown in FIG. 9a, the fluid chamber areas of the walls 46 and 48 are offset when the fluid chamber 54 has no volume.

The wall extensions 60 and 62 may be formed together with the walls 46 and 48, respectively, or the wall extensions 60 and 62 may be separate components which are rigidly attached to the walls 46 and 48 such as rigid or stiff cables, wires, or plates. The wall extension 62 is shown as being attached to the heel of the prosthetic foot 6. Wall extensions 60, 62 may be rearranged such that wall extension 60 is attached to the heel portion of the prosthetic foot 6, and wall extension 62 is attached to the proximal portion of the prosthetic foot 6.

The compression transfer element includes the wall extension 62 attached to or integrated with the wall 48. When a compressive force in the direction 56 occurs such as during a heel strike, the volume of the fluid chamber 54 increases by having at least the wall extension 62 push or shift the movable wall 48 diagonally away from movable wall 46 to increase the volume between the two movable walls 46 and 48. The movement of the walls 46 and 48 is guided by the hinges 50 and 52. The direction of the fluid chamber expansion 58 may also be substantially perpendicular to the compressive force 56.

After the heel strike, a compression element such as an elastomer or a spring system compresses the pump 44 by reducing the volume of the fluid chamber 54 to being zero or near zero and returns the pump 44 to the state shown in FIG. 9a.

Similar to the previous embodiments, the input port and output port of the fluid chamber 54 may be located on any surface of the pump.

The vacuum pump 44 may comprise two pairs of opposing parallel walls. The first pair of walls may have a placement similar to those of movable walls 46 and 48. The second pair of walls may be parallel to the hinges 50 and 52.

As shown in FIG. 9b, the vacuum pump 44 may have a rectangular cross-section. The vacuum pump 44 may also have a fluid chamber 54 with a diamond cross-section.

Figure 10:
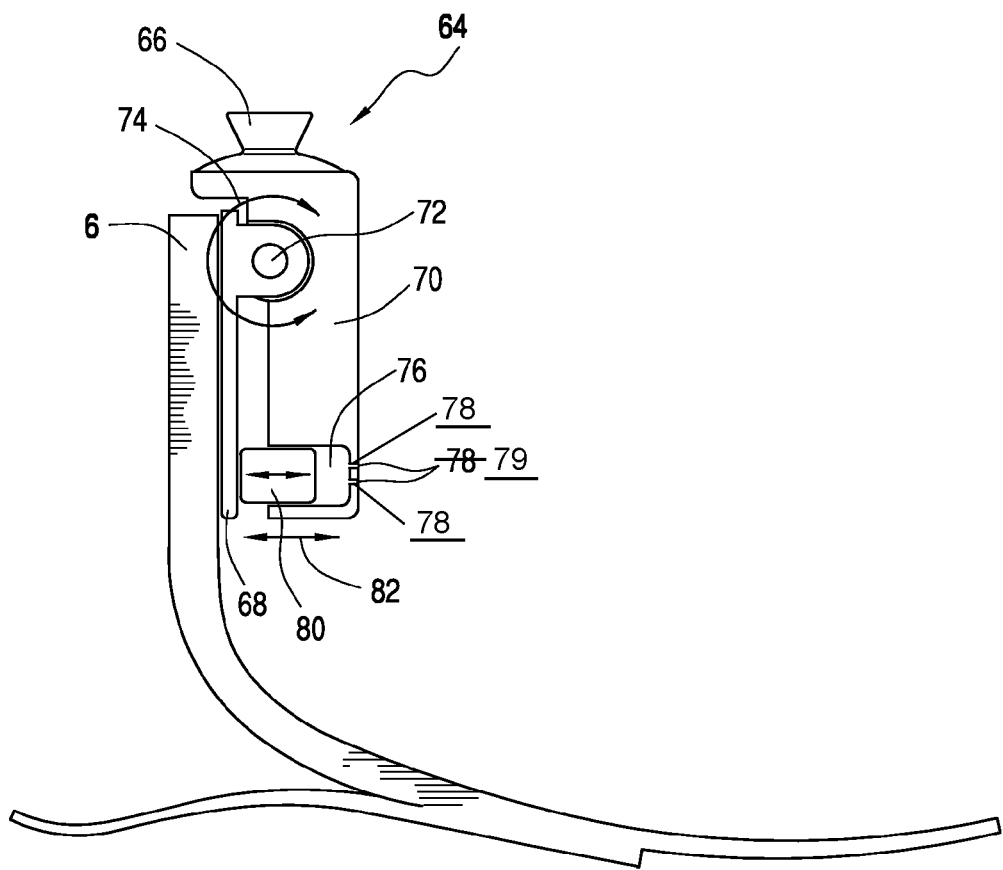
FIG. 10 is a side view of a fourth embodiment of the prosthetic system.

FIG. 10 shows a side view of another embodiment of the vacuum assisted suspension system including a vacuum pump 64 on a prosthetic foot 6. The vacuum pump 64 functions through a pivoting mechanism. The pivoting mechanism generally involves a base member and a pivoting member that pivot about or rotate around a common joint to cause a protruding wall or piston to reciprocate within a fluid chamber. The base member and the pivoting member are arranged such that the rotation occurs between the prosthetic foot and the residual limb. In this manner, the pivoting of the pump helps make the gait process smoother by functioning similar to a regular heel. Thus, the fourth embodiment is advantageous in that the fourth embodiment aids the gait of the user and also assists in maintaining negative pressure in the sealed cavity of a socket.

In the embodiment shown in FIG. 10, the vacuum pump 64 has a connector 66 on the proximal end to connect the pump 64 to, for example, a pylon or in the end a residual limb. The pump 64 further includes an elongate base member 68, an elongate pivoting member 70, a joint 72, a fluid chamber 76, and a protruding wall or piston 80. The base member 68 is affixed to a portion of the prosthetic foot 6 preferably the shin area of the foot 6, and the connector 66 is attached to the pivoting member 70 such that the prosthetic foot 6 pivots separately from the pylon and the residual limb. Near the proximal end of the base member 68 is a joint 72 which connects the base member 68 to the pivoting member 70. The joint 72 enables the base member 68 and the pivoting member 70 to rotate or pivot with respect to each other in the direction shown by arrow 74. The joint 72 may be in the form of two partial elements such as a cylindrical pin on one member inserted through a pin holder of the other member. The pivoting or rotation of the base member 68 and the pivoting member 70 preferably occurs in a plane parallel to the anterior-posterior plane. The axis of rotation for the joint 72 is preferably perpendicular to the anterior-posterior plane.

At the end opposite the joint 72 which is shown as the distal end in FIG. 10, the base member 68 has a protruding wall or piston 80 positioned opposite to a recess in the pivoting member 70. The protruding wall or piston 80 is received within the recess, and the protruding wall 80 forms a seal with the interior of the recess. Together the protruding wall 80 and the recess form a fluid chamber 76. The fluid chamber 76 is preferably located at the opposite end of the joint 72 or the distal end of the pump 64 to maximize the difference between the maximum and minimum volume of the fluid chamber 76. Arrow 80 shows the direction of reciprocation of the piston 80 within the recess of the pivoting member 70. Arrow 82 which is parallel to arrow 80 represents the overall direction of expansion and contraction of the fluid chamber 76. When the base member 68 and the pivoting member 70 are rotated towards each other, the piston 80 is inserted deeper within the recess causing the volume of the fluid chamber 76 to decrease. When the base member 68 and the pivoting member 70 are rotated away from each other, the piston 80 is pulled away from the interior of the recess and causes the volume of the fluid chamber 76 to increase.

The fluid chamber 76 has openings 78 which are preferably connected to one-way valves 79 to control the direction of fluid flow into and out of the chamber. For example, one opening may be connected to a one-way valve 79 which only allows fluid into the fluid chamber 76. This valve 79 is in fluid communication with the cavity of the socket to increase the vacuum or negative pressure within a sealed socket cavity. The other opening is connected to a one-way valve 79 which only allows fluid to be expelled from the fluid chamber 76, for example, to atmosphere.

During gait such as at heel strike, the base member 68 and the pivoting member 70 rotate away from each other to cause an expansion of the fluid chamber 76 and an increase of the volume of the fluid chamber 76 which draws fluid into the pump 64 from the socket cavity. After the toe off, the base member 68 and pivoting member 70 rotate towards each other to decrease the volume of the fluid chamber 76 and expel fluid out of one of the openings. The rotation of the base member 68 and pivoting member 70 towards each other may be accomplished with a spring element or other element which applies an external force.

Similar to the other embodiments described herein, the fluid chamber 76 of the vacuum pump 64 preferably has minimum volume of zero or approximately zero such that during gait, any fluid drawn into fluid chamber 76 in one cycle is substantially expelled before more fluid is drawn into the fluid chamber 76.

The resistance of the joint 72 is adjustable to increase or decrease the amount of rotational force required to pivot the base member 68 and the pivoting member 70 based on the user's preference. The angle of the pump 64 and the degree with which the member 68, 70 are able to rotate is also adjustable to accommodate different situations such as different shoes.

The embodiments described herein may be used with an exemplary prosthetic socket as described in U.S. Pat. No. 7,427,297 issued Sep. 23, 2008 incorporated herein by reference and belonging to the assignee of this disclosure.

The embodiments described herein may be used with an exemplary prosthetic foot as described in U.S. Pat. No. 6,969,408 issued Nov. 29, 2005 incorporated herein by reference and belonging to the assignee of this disclosure.

The embodiments described herein may be used with a pressure regulator to insure the safety and comfort of the user which may be achieved using mechanical and/or electronic methods known in the industry.

While the foregoing embodiments have been described and shown, it is understood that alternatives and modifications of these embodiments, such as those suggested by others, may be made to fall within the scope of the invention. Any of the principles described herein may be extended to other types of prosthetic or orthopedic devices.

The invention claimed is:

1. A vacuum assisted suspension system for a prosthetic system including a prosthetic socket, comprising:
 a prosthetic foot; and
 a pump mechanism connected to the prosthetic foot and fluidly couplable to a prosthetic socket, the pump mechanism including:
  a pivoting member having an elongate configuration rotatable relative to the prosthetic foot about a joint and including a distal end portion defining a recess;
  a piston connected to the prosthetic foot and movably received in the recess; and
  a fluid chamber defined between an end of the piston and an interior of the recess, wherein when no weight is placed on the prosthetic foot a volume of the fluid chamber is zero or near-zero and when weight of a user is placed on the prosthetic foot during a heel strike the pivoting member rotates away from the piston and expands the volume of the fluid chamber to draw fluid into the fluid chamber from the prosthetic socket.

2. The system of claim 1, wherein pivoting member and the prosthetic foot are biased to rotate toward one another.

3. The system of claim 1, wherein the joint is arranged to provide a resistance to rotation of the pivoting member about the joint.

4. The system of claim 3, wherein the resistance is adjustable to vary an amount of rotational force required to rotate the pivoting member about the joint.

5. The system of claim 1, wherein the joint is located toward a proximal end portion of the pivoting member.

6. The system of claim 1, wherein the joint connects the pivoting member to a base member attached to the prosthetic foot.

7. The system of claim 6, wherein the base member carries the piston.

8. The system of claim 7, wherein the piston comprises a protruding wall defined on the base member.

9. The system of claim 8, wherein the protruding wall is located opposite the joint on the pivoting member.

10. The system of claim 1, wherein the pivoting member includes a prosthetic connector.

11. The system of claim 1, wherein the pivoting member defines at least one opening in fluid communication with the fluid chamber.

12. The system of claim 11, wherein the at least one opening includes a one-way valve.

13. The system of claim 1, wherein rotating the pivoting member away from the prosthetic foot expands the volume of the fluid chamber.

14. The system of claim 1, wherein rotating the pivoting member toward the prosthetic foot decreases the volume of the fluid chamber.

15. A prosthetic system comprising:
 a prosthetic socket;
 a prosthetic foot including a heel member and connected to the prosthetic socket; and
 a pump mechanism connected to the prosthetic foot and fluidly coupled to the prosthetic socket, the pump mechanism including:
  a pivoting member having an elongate configuration rotatable relative to the prosthetic foot about a joint and including a distal end portion defining a recess;
  a piston connected to the prosthetic foot and movably received in the recess; and
  a fluid chamber defined between an end of the piston and an interior of the recess, wherein when no weight is placed on the prosthetic foot a volume of the fluid chamber is zero or near-zero and when weight of a user is placed on the heel member during a heel strike the pivoting member rotates away from the piston and expands the volume of the fluid chamber to draw fluid into the fluid chamber from the prosthetic socket.

16. The system of claim 15, wherein the joint is located toward a proximal end portion of the pivoting member.

17. The system of claim 15, wherein the joint connects the pivoting member to a base member attached to the prosthetic foot.

18. The system of claim 15, wherein the base member carries the piston.

19. A vacuum assisted suspension system for a prosthetic system including a prosthetic socket, comprising:
 a prosthetic foot; and
 a pump mechanism connected to the prosthetic foot and fluidly couplable to a prosthetic socket, the pump mechanism including:
 a base member attached to the prosthetic foot;
 a pivoting member having an elongate configuration rotatable relative to the prosthetic foot about a joint and including a distal end portion defining a recess;
 a piston defined by the base member and movably received in the recess; and
 a fluid chamber defined between an end of the piston and an interior of the recess, wherein when no weight is placed on the prosthetic foot a volume of the fluid chamber is zero or near-zero and when weight of a user is placed on prosthetic foot during a heel strike the pivoting member pivots away from the piston and expands the volume of the fluid chamber to draw fluid into the fluid chamber from the prosthetic socket.

* * * * *